Figure 1:
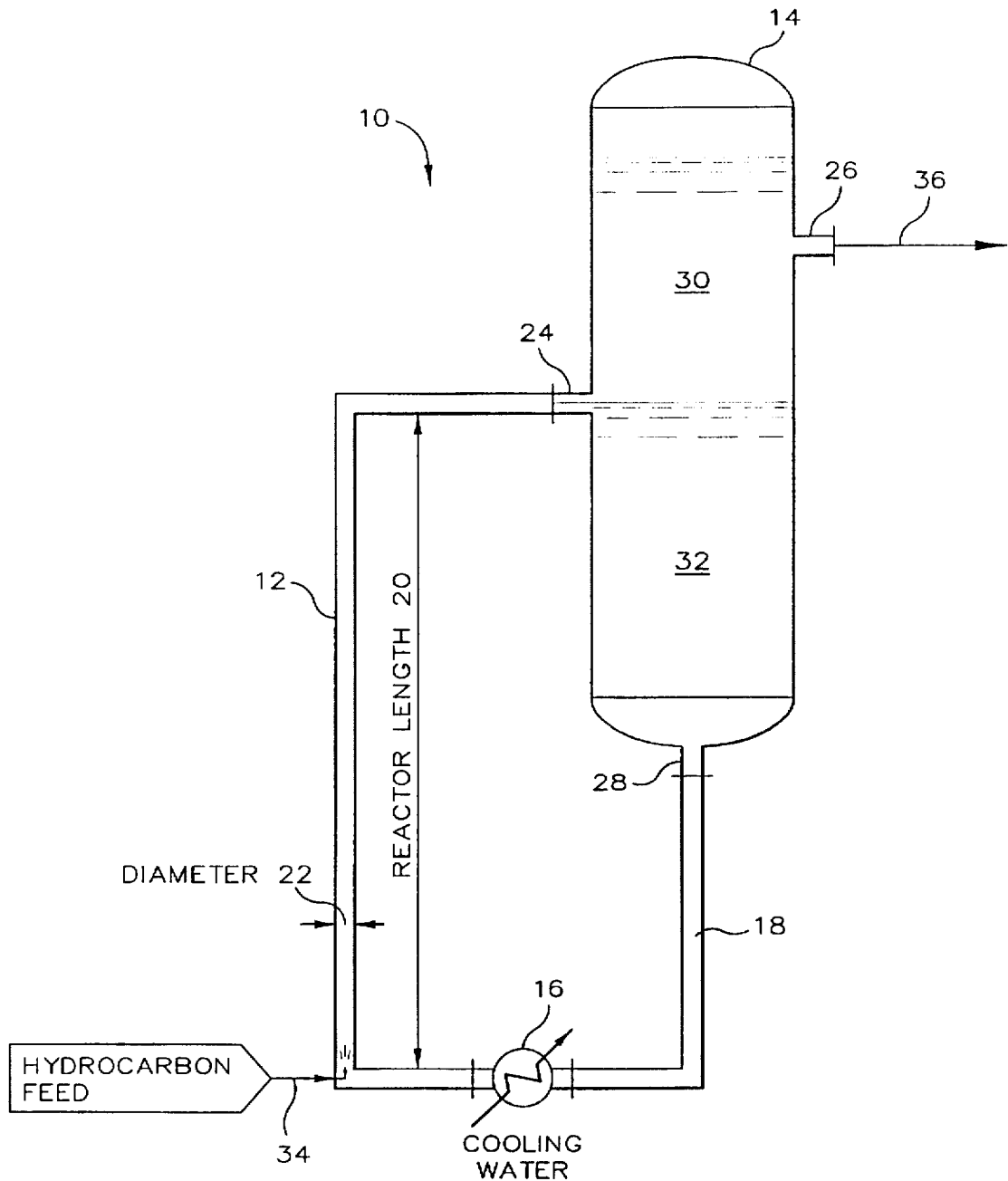

United States Patent [19]
Randolph et al.

[11] Patent Number: 5,792,896
[45] Date of Patent: Aug. 11, 1998

[54] ISOPARAFFIN-OLEFIN ALKYLATION

[75] Inventors: Bruce B. Randolph; Richard L. Anderson; Harvey D. Hensley, all of Bartlesville, Okla.

[73] Assignee: Phillips Petroleum Company, Bartlesville, Okla.

[21] Appl. No.: 808,778

[22] Filed: Mar. 4, 1997

Related U.S. Application Data

[63] Continuation-in-part of Ser. No. 990,335, Dec. 11, 1992, abandoned.

[51] Int. Cl.[6] .................................. C07C 2/62; C07C 2/60
[52] U.S. Cl. ........................................ 585/724; 585/730
[58] Field of Search ................................ 585/723, 724, 585/730, 921, 922, 924

[56] References Cited

U.S. PATENT DOCUMENTS

| | | | |
|---|---|---|---|
| 2,407,136 | 9/1946 | Clarke | 260/683.4 |
| 3,080,438 | 3/1963 | Sailors | 260/683.48 |
| 3,158,661 | 11/1964 | Plaster et al. | 260/683.48 |
| 3,169,153 | 2/1965 | Walker et al. | 260/683.48 |
| 3,213,157 | 10/1965 | Hays et al. | 260/683.48 |
| 3,233,007 | 2/1966 | Chapman | 260/683.48 |
| 3,253,054 | 5/1966 | Pool | 260/683.48 |
| 3,281,213 | 10/1966 | Waddill | 23/285 |
| 3,795,712 | 3/1974 | Torck | 260/671 |
| 4,058,575 | 11/1977 | Cahn et al. | 260/666 P |
| 4,161,497 | 7/1979 | Makovec | 585/714 |
| 4,276,257 | 6/1981 | Dixon et al. | 422/62 |
| 4,317,795 | 3/1982 | Makovec et al. | 422/62 |
| 4,863,697 | 9/1989 | Hann et al. | 422/110 |
| 5,146,036 | 9/1992 | Hovis | 585/723 |
| 5,191,156 | 3/1993 | Joryensen et al. | 588/249 |

FOREIGN PATENT DOCUMENTS

| | | |
|---|---|---|
| 882644 | 11/1961 | United Kingdom . |
| 93/00316 | 1/1993 | WIPO . |

Primary Examiner—Glenn Caldarola
Assistant Examiner—Thuan D. Dang
Attorney, Agent, or Firm—Charles W. Stewart

[57] ABSTRACT

An alkylation process for reacting alkylatable hydrocarbons in the presence of a sulfolane and hydrofluoric acid catalyst within a natural circulation reaction and circulation system.

33 Claims, 1 Drawing Sheet

ISOPARAFFIN-OLEFIN ALKYLATION

This is a continuation-in-part of application Ser. No. 07/990,335, filed Dec. 11, 1992 now abandoned.

The present invention relates to the catalytic alkylation of hydrocarbons. In one aspect it relates to an alkylation system in which cyclic flow of alkylation catalyst is provided. In another aspect it relates to an improved process for the production of alkylate product by contacting hydrocarbon with a sulfolane and HF catalyst composition.

One of the major problems associated with the catalytic alkylation of hydrocarbons lies in the handling of the alkylation catalyst, that is, transporting the catalyst to the various parts of the reaction and recovery system. The problem is particularly aggravated when acid catalysts such as hydrofluoric acid are used since these materials in many instances are highly corrosive to ordinary materials of construction. Special equipment such as alloy valves and vessels, special pumps and pump packings are required and special safety precautions are necessary in the alkylation of hydrocarbons with these acid catalysts.

One proposed solution to some of the problems associated with the handling of hydrofluoric acid as an alkylation catalyst has been the use of a suitable diluent that does not have a negative effect upon the ultimate alkylate end-product. Such diluents can include sulfone compounds and particularly sulfolane. Mixtures comprising sulfolane and hydrofluoric acid have been found to be suitable alkylation catalysts when utilized in batch reactions in which the contact times are prolonged. It is desirable, however, to utilize cyclic or natural circulation alkylation systems because of the safety aspects of such systems, but prior to the discovery of the herein described inventive process, it was uncertain as to whether an alkylation catalyst comprising sulfolane and hydrogen fluoride would have acceptable physical properties which permit its use in a cyclic alkylation system. It was uncertain as to whether the reaction kinetics of the alkylation of olefin hydrocarbons by isoparaffin hydrocarbons in the presence of a sulfolane and hydrogen fluoride catalyst would permit the use of a cyclic flow alkylation system.

It is thus an object of this invention to provide a process for the catalytic alkylation of hydrocarbons utilizing a cyclic flow alkylation system.

The inventive process includes reacting a mixture of olefin hydrocarbons and paraffin hydrocarbons within a reaction zone, having a lower portion, an upper portion, and a volume, in the presence of a sulfolane and hydrofluoric acid catalyst. This alkylation process includes introducing the hydrocarbon mixture into the lower portion of the reaction zone which contains the sulfolane and hydrofluoric acid catalyst and passing the resultant alkylate reaction effluent, which includes hydrocarbons and the catalyst, from the upper portion of the reaction zone to a settling zone. Within the settling zone, a phase separation occurs so as to produce a hydrocarbon phase and a catalyst phase. The catalyst phase is cooled to produce a cooled catalyst which is then utilized as the catalyst contained within the reaction zone.

Other objects and advantages of the invention will be apparent from the detailed description of the invention, the appended claims, and the drawing in which:

FIG. 1 is a diagrammatic illustration of the cyclic flow alkylation system having an alkylation reactor, settler vessel, heat exchanger, and a return.

It has unexpectedly been found that a natural circulation liquid lift system having a reaction zone, a settling zone, a heat transfer zone and a return is operable for the catalytic alkylation of hydrocarbons when a catalyst mixture comprising sulfolane and hydrogen fluoride is used. The operability of such a lift system is highly dependent on such factors as the physical properties of the alkylation catalyst used, the alkylation reaction kinetics and the geometry of the alkylation lift system. The physical properties of the alkylation catalyst used in the alkylation process greatly affects the operation of the lift system due to its dependence upon the density differentials between a hydrocarbon feedstock and a catalyst to furnish the motive power for promoting circulation. The primary motive power can come from the kinetic energy of the inlet hydrocarbon stream charged to the reaction zone, but preferably, it comes from the effect of the difference in density of the flowing streams. In the mixed hydrocarbon stream, the average stream density is lower than the density of the cycling stream so a differential static pressure is established which is proportional to the total elevation of the two flowing streams. In order for the system to arrive at a steady state, the cycling streams must develop a pressure drop equal to the static pressure head developed plus the kinetic head obtained from the inlet motive stream. It is possible to use the heavier liquid as the motive stream if one desires a downward flowing mixed phase stream.

The reaction kinetics of the alkylation reaction within the reaction zone of the lift system can critically impact its operability. Principally, the rate at which the alkylation reaction proceeds within a reaction zone is determinative of the particular reaction system design and its geometry. Because of the impact that the reaction rate has on the operability of the natural circulation lift system, prior to the discovery of the herein described inventive process, it was unknown that catalytic alkylation of hydrocarbons utilizing a sulfolane and hydrogen fluoride catalyst would work within a natural circulation lift system. In fact, the physical properties, which include catalytic properties, of a sulfolane and hydrogen fluoride catalyst mixture are different enough from other conventional or known alkylation catalysts that individuals skilled in the art of catalytic alkylation could not predict that such a catalyst mixture would perform in a natural circulation system.

However, it has been discovered that a natural circulation lift system can operate with a sulfolane and hydrogen fluoride catalyst mixture in the alkylation of hydrocarbons provided the system includes certain critical geometric dimensions and the process conditions are such as to allow the completion of the alkylation reactions within the alkylation zone of the lift system. It has been discovered that the contact time for hydrocarbon reactants within the reaction zone, and in the presence of the alkylation catalyst, should be sufficient to provide for essentially complete conversion of the olefin reactant in the reaction zone of the system. Thus, the required contact time can impact the geometry of the lift system, particularly the reactor dimensions.

The term "contact time" can be defined as the length of time the hydrocarbon reactants and the catalyst are in intimate contact in the reaction zone. It has been discovered that for a natural circulation lift system having a geometry as described herein, the contact time generally should exceed about 5 seconds. Preferably, however, the contact time can be at least about 10 seconds; and, most preferably, the contact time is at least 20 seconds.

A required contact time greatly impacts the geometric design of the natural circulation lift system and necessarily requires that the dimensions of the reaction zone be such that the contact time of the alkylatable hydrocarbons within the reaction zone and in which they are in contact with the alkylation catalyst is sufficient to allow the completion of the alkylation reactions. Also, however, the geometric dimensions of the reaction zone must be such as to permit the natural circulation within the lift system of the catalyst and hydrocarbons. The required dimensions of the reaction zone of a natural circulation lift system are not readily obvious to one skilled in the art due to the uniqueness of the physical properties of the alkylation catalyst; particularly, the properties of a sulfolane and hydrogen fluoride catalyst.

Examples of other factors which impact the dimensions of the reaction zone include such factors as the relative density between the hydrocarbon feedstock and catalyst, the viscosity of the catalyst, and alkylation reaction. It has been determined that to provide for the natural circulation of the catalyst and hydrocarbon reactants within a reaction zone having an approximate circular flow area, the reaction zone should generally be elongated or extended in the vertical direction and have a lower portion and an upper portion with the ratio of the vertical length of the reaction zone to the nominal diameter of the reaction zone exceeding about 5 to 1. When referring herein to the diameter or the nominal diameter of the reaction zone, these terms are defined as being the ratio of the cross sectional area of the flow area of the reaction zone to the length of the wetted perimeter of the reaction zone multiplied by a factor of four (4). The preferred length-to-diameter ratio of the reaction zone is greater than about 7.5 to 1 and, most preferably, the length-to-diameter ratio is greater than 10 to 1.

The hydrocarbon feed is introduced into the lower portion of the reaction zone defined by the riser-reactor and which contains the alkylation catalyst. Any means suitable for introducing the feed into the reaction zone can be used which includes the use of constricted passageway, or feed nozzles, of small cross-section relative to the interior cross-section of the reaction zone. The feed nozzles assist in forming small droplets of the hydrocarbon feed which provides for the maintenance of a high interfacial area during their life in the reactor. A high rate of reaction requires the maintenance of a high interfacial area. The direction of flow of the liquid hydrocarbons in relation to the direction of flow of the liquid catalyst is also important. The catalyst flow path must be established in the same direction as the hydrocarbon feed at the point of initial contact with the liquid hydrocarbon. By this method and apparatus there is no sustained build-up of catalyst or hydrocarbon or catalyst mixture at the point of contact such as would be the case if the catalyst were introduced above the point of introduction of the hydrocarbons or if the catalyst were introduced at right angles to the direction of flow of the hydrocarbon. Also, by introducing a high velocity stream of flowing hydrocarbons into a stream of acid catalyst flowing in the same direction, the droplets of liquid reactants retain their small size while flowing upwardly with the catalyst phase thereby maintaining their high interfacial area. Further, as confirmed by Bernoulli's Theorem, the use of a high velocity results in a lower static pressure which permits improved penetration of the one phase in the other phase. Further, by maintaining a high interfacial area and by eliminating the stagnant pool, there is minimum of undesirable side reactions. Preferably these constricted passageways or tubes have a diameter sufficient to provide a differential velocity between the upwardly flowing hydrocarbons and upwardly flowing catalyst of 15 to 35 feet per second. Preferably these tubes have an internal diameter of ¼" to ¾".

The alkylation catalyst utilized in the inventive process can comprise, consist of, or consist essentially of a hydrogen halide component and a sulfolane component. The hydrogen halide component of the catalyst composition or catalyst mixture can be selected from the group of compounds consisting of hydrogen fluoride (HF), hydrogen chloride (HCl), hydrogen bromide (HBr), and mixtures of two or more thereof. The preferred hydrogen halide component, however, is hydrogen fluoride, which can be utilized in the catalyst composition in anhydrous form, but, generally, the hydrogen fluoride component utilized can have a small amount of water. The amount of water present in the hydrogen fluoride and sulfolane mixture in no event can be more than about 30 weight percent of the total weight of the hydrogen fluoride component, which includes the water, and preferably, the amount of water present in the hydrogen fluoride component is less than about 10 weight percent. Most preferably, the amount of water present in the hydrogen fluoride component is less than 5 weight percent. When referring herein to the hydrogen halide component, or more specifically to the hydrogen fluoride component of the catalyst composition of the invention, it should be understood that these terms mean either the hydrogen halide component as an anhydrous mixture or a mixture that includes water. The references herein to weight percent water contained in the hydrogen halide component means the ratio of the weight of water to the sum weight of the water and hydrogen halide multiplied by a factor of 100 to place the weight ratio in terms of percent.

In a continuous alkylation process such as described herein the catalyst phase can become further diluted as a result of the accumulation of alkylation reaction by-product such as acid soluble oils. Acid soluble oils (ASO) are conjunct polymers which are highly olefinic oils produced by acid-catalyzed reactions of hydrocarbons. An extensive description and characterization of certain types of conjunct polymer oils is provided in the *Journal of Chemical and Engineering Data* article entitled "Molecular Structure of Conjunct Polymers" pages 150–160, Volume 8, Number 1, by Miron and Lee. This article is incorporated herein by reference. The physical properties of ASO depend upon the particular hydrocarbon feed processed, the catalyst utilized in the process, feed contaminants such as hydrogen sulfide, butadiene, oxygenates and other compounds, and the alkylation process reaction conditions. Thus, as the term is used herein, ASO will be those conjunct polymers produced as a by-product in the catalyzed reaction of mono-olefins with isoparaffins utilizing a catalyst mixture containing a hydrogen halide component.

It is important to the proper operation of the inventive process herein for the ASO concentration in the hydrogen halide and sulfolane catalyst mixture to not exceed 8 weight percent of the catalyst mixture due to the detrimental effects the ASO can have on catalyst performance. It is preferred, however, for the ASO concentration to be less than about 6 weight percent. Because of certain benefits that the presence of ASO in the catalyst mixture may have on the catalyst performance, it can be desirable to have a small concentration of ASO in the catalyst mixture. Thus, it is desirable to have a concentration of ASO from 0.4 weight percent up to 8 weight percent, and preferably, between 0.5 and 6 weight percent.

Generally, those skilled in the art of hydrogen fluoride catalyzed olefin alkylation processing have known that to obtain the highest quality of alkylate from the aforementioned olefin alkylation process, it is essential for the hydrogen fluoride catalyst to be as free from contaminating compounds as is feasible. It is generally known that small amounts of other compounds contained in the hydrogen fluoride catalyst of an olefin alkylation process can have detrimental effects upon product alkylate quality by negatively affecting the selectivity of the alkylation reaction toward the production of more desirable end-product. such as, for example, trimethylpentanes (TMP) in the case of the alkylation of butylenes by isobutane. It is further known to those skilled in the art that small amounts of components contained in a hydrogen fluoride alkylation catalyst can have a negative impact upon its activity toward the alkylation of olefins.

Based upon the known effects of hydrogen fluoride catalyst contaminants upon the activity and selectivity of the alkylation process toward the production of high quality alkylate, one skilled in the art would expect that the addition of small to large amounts of sulfolane to a hydrogen fluoride catalyst would have an enormously detrimental effect upon its catalytic performance. However, it has been discovered that the presence of small quantities of sulfolane in combination with hydrogen fluoride will have little negative impact on the performance of the resultant mixture as an alkylation catalyst, and, it has further been discovered that instead of having a detrimental impact upon the catalytic performance, a small concentration in an amount less than about 30 weight percent of the sulfolane component in combination with the hydrogen fluoride can in certain instances enhance the performance of the resultant composition as an alkylation process catalyst.

It is, therefore, desirable to utilize sulfolane in the catalyst mixture in an amount in the range of from about 2.5 weight percent to about 50 weight percent. To achieve optimal benefits from the catalyst composition, the preferred catalyst mixture should contain the sulfolane component in the range of from about 5 weight percent to about 40 weight percent and, more preferably, the sulfolane concentration shall range from 10 to 30 weight percent. While the most preferred sulfolane concentration for optimal catalytic benefit is in the range of from 10 to 30 weight percent, an effective catalyst can have from 10 to 50 weight percent sulfolane. When referring herein to the weight percent of the sulfolane component of the catalyst mixture of hydrogen fluoride and sulfolane, the term weight percent is defined as the ratio of the weight of sulfolane to the sum weight of sulfolane and hydrogen fluoride multiplied by a factor of one hundred (100).

The alkylation process of the present invention processes mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

In order to improve selectivity of the alkylation reaction toward the production of the desirable highly branched aliphatic hydrocarbons having seven or more carbon atoms, a substantial stoichiometric excess of isoparaffin hydrocarbon is desirable in the reaction zone. Molar ratios of isoparaffin hydrocarbon to olefin hydrocarbon of from about 2:1 to about 25:1 are contemplated in the present invention. Preferably, the molar ratio of isoparaffin-to-olefin will range from about 5 to about 20; and, most preferably, it shall range from 8 to 15. It is emphasized, however, that the above recited ranges for the molar ratio of isoparaffin-to-olefin are those which have been found to be commercially practical operating ranges; but, generally, the greater the isoparaffin-to-olefin ratio in an alkylation reaction, the better the resultant alkylate quality.

Isoparaffin and olefin reactant hydrocarbons normally employed in commercial alkylation processes are derived from refinery process streams and usually contain small amounts of impurities such as normal butane, propane, ethane and the like. Such impurities are undesirable in large concentrations as they dilute reactants in the reaction zone, thus decreasing reactor capacity available for the desired reactants and interfering with good contact of isoparaffin with olefin reactants. Additionally, in continuous alkylation processes wherein excess isoparaffin hydrocarbon is recovered from an alkylation reaction effluent and recycled for contact with additional olefin hydrocarbon, such nonreactive normal paraffin impurities tend to accumulate in the alkylation system. Consequently, process charge streams and/or recycle streams which contain substantial amounts of normal paraffin impurities are usually fractionated to remove such impurities and maintain their concentration at a low level, preferably less than about 5 volume percent, in the alkylation process.

Alkylation reaction temperatures within the contemplation of the present invention are in the range of from about 0° F. to about 150° F. Lower temperatures favor alkylation reaction of isoparaffin with olefin over competing olefin side reactions such as polymerization. However, overall reaction rates decrease with decreasing temperatures. Temperatures within the given range, and preferably in the range from about 30° F. to about 130° F., provide good selectivity for alkylation of isoparaffin with olefin at commercially attractive reaction rates. Most preferably, however, the alkylation temperature should range from 50° F. to 100° F.

Reaction pressures contemplated in the present invention may range from pressures sufficient to maintain reactants in the liquid phase to about fifteen (15) atmospheres of pressure. Reactant hydrocarbons may be normally gaseous at alkylation reaction temperatures, thus reaction pressures in the range of from about 40 pounds gauge pressure per square inch (psig) to about 160 psig are preferred. With all reactants in the liquid phase, increased pressure has no significant effect upon the alkylation reaction.

Referring now to FIG. 1, depicted is natural circulation lift system 10 comprising riser-reactor 12, settler vessel 14, heat exchanger 16 and return conduit 18 all of which are operatively connected in series and in fluid flow communication to define a cyclic flow path for an alkylation catalyst. Riser-reactor 12 is a vertically elongated tubular reactor having a lower portion and an upper portion and which defines a reaction zone wherein is contained the alkylation catalyst. Riser-reactor 12 also has a reactor length 20 and a diameter 22 with a ratio of length to diameter exceeding about 5 to 1.

Settler vessel 14 is equipped with inlet 24 for receiving alkylate reaction effluent, product outlet 26 for the removal of product, and bottom outlet 28 for returning separated catalyst to riser-reactor 12. Settler vessel 14 defines a separation zone and provides means for receiving and separation of an alkylation reaction effluent into a separate hydrocarbon phase 30 and a separate catalyst phase 32. Thus, the upper end of riser-reactor 12 is operatively connected to and is in open communication with inlet 24, and the lower end of riser-reactor 12 is operatively connected to and is in fluid flow communication with return conduit 18.

Return conduit 18 is also operatively connected to and is in open communication with bottom outlet 28 to thereby provide a circuit or cyclic path for the natural circulation of catalyst within natural circulation lift system 10. Interposed in return conduit 18 is heat exchanger or catalyst cooler 16, which defines a cooling zone and provides means for removing energy from the catalyst by indirect heat exchange with a heat transfer fluid such as cooling water. Conduit 34 is provided for introducing a hydrocarbon feed mixture into the lower portion of riser-reactor 12. Conduit 36 is operatively connected to product outlet 26 and provides for the conveyance of separate hydrocarbon phase 30 from settler vessel 14 to downstream processing.

In the operation of natural circulation lift system 10, a liquid hydrocarbon feed material comprising an alkylatable hydrocarbon, such as a low boiling olefin and an alkylating agent, such as a low boiling isoparaffin, admixed in suitable proportions, is introduced through conduit 34, passing upwardly through riser-reactor 12 as a plurality of high velocity streams of small cross-section. Initially, riser-reactor 12 contains a quantity of alkylation catalyst such that the level of catalyst extends a substantial distance up into the reaction zone defined by riser-reactor 12. The hydrocarbon feed entering the reaction zone separates into small droplets which pass upwardly through riser-reactor 12. The catalyst present in the reaction zone and additional catalyst from conduit 18, pass upwardly through riser-reactor 12 in co-current flow with the hydrocarbon feed charged through conduit 34. The simultaneous upward movement of acid and hydrocarbon results from a combination of (1) the kinetic energy of the hydrocarbon feed, and (2) the difference in density of the catalyst-hydrocarbon mixture in riser-reactor 12 as compared to the density of separate catalyst phase 32. As the catalyst and hydrocarbon reactants come into contact, reaction between the olefin and isoparaffin occurs, with the formation of higher molecular weight materials of increased octane value. With the alkylation reaction being exothermic, the temperature of the catalyst and reactants increases as the reaction mixture moves upwardly through the riser-reactor 12. Within a period of time, usually on the order of greater than about 5 seconds, the alkylation reaction is completed, after which time reaction effluent containing hydrocarbon product (alkylate), catalyst and unreacted feed hydrocarbons passes from riser-reactor 12 entering settler vessel 14 through inlet 24.

Separation of the alkylation reaction effluent into catalyst and hydrocarbon phases, which commences with introduction of the reaction effluent to settler vessel 14 is substantially completed by the time the effluent is introduced into said vessel. Settler vessel 14 can be operated liquid full by the use of elevated pressures or it can be operated with both liquid and gas phases at lower pressures, with provision being made to vent excess gas. The upper phase or separated hydrocarbon phase 30 is withdrawn from settler vessel 14 through conduit 36 and yielded for further treatment including fractionation (not shown) as required. The lower phase or separated catalyst phase 32 passes from settler vessel 14 downwardly through conduit 18 and is introduced to heat exchanger 16. Catalyst passing through the heat exchanger is reduced in temperature sufficiently to remove heat picked up during the alkylation reaction.

The following example demonstrates the advantages of the present invention. This example is by way of illustration only, and is not intended as a limitation upon the invention as set out in the appended claims.

EXAMPLE I

This example demonstrates that a riser-reactor alkylation system can be successfully utilized in the alkylation of olefins when a mixture of hydrogen fluoride and sulfolane is used as a catalyst. Also demonstrated is the importance of reactor geometry and contact time to the successful operation of a natural circulation reactor system.

A laboratory scale riser-reactor was used to obtain reaction data for the alkylation of olefins within such a reactor. The riser-reactor included a 2-foot section of 1-inch monel schedule 40 pipe that was equipped with a coolant jacket for heat transfer to maintain a fixed reactor temperature of about 90° F. Provided in the bottom end of the riser-reactor was a feed nozzle for introducing hydrocarbon feed into the riser-reactor which contained a measured amount of a liquid catalyst mixture of sulfolane and hydrofluoric acid. To adjust the contact time that the hydrocarbon feed was in contact with the catalyst within the riser-reactor, the amount of catalyst contained therein in each experimental run was adjusted while maintaining the feed rate substantially fixed. Feed was continuously charged to the riser-reactor for a period of time with the reactor effluent being continuously removed from the top of the riser-reactor. At periodic time intervals, samples of the reactor effluent were taken for gas chromatographic analysis. The resultant data are presented in Tables I, II, III, IV, V, and VI.

Tables I and II present data for the experimental alkylation process which uses a catalyst mixture of 80 percent HF and 20 percent sulfolane at two different feed contact times which were adjusted by respectively utilizing 300 ml of catalyst and 100 ml of catalyst. Tables III and IV present data for the experimental alkylation process using a catalyst mixture of 60 percent HF and 40 percent sulfolane at two different feed contact times adjusted by respectively utilizing 300 ml of catalyst and 100 ml of catalyst. Tables V and VI present data for the experimental alkylation process using a catalyst mixture of 50 percent HF and 50 percent sulfolane at two different feed contact times adjusted by respectively utilizing 300 ml of catalyst and 200 ml of catalyst. The data presented in Tables I-VI demonstrate that two factors which impact the quality of the alkylate end-product are contact time and catalyst composition. For a given feed contact time, the catalyst performance and alkylate quality declines as the fraction of the hydrofluoric acid component of the catalyst mixture decreases to below about 60 percent. This is demonstrated by such factors as a reduction in olefin conversion, alkylate octane, trimethylpentane-to-dimethylhexane ratio in the alkylate end-product and with increases in the undesirable fluoride and $C^+$ components of the alkylate end-product. On the other hand, the data also demonstrate that catalyst performance and alkylate quality improve with increases in contact time. In a natural circulation alkylation reaction system, the geometry of its riser-reactor element will impact the contact time and, therefore, the geometry becomes an important aspect of the system design.

TABLE I

| Time, Hrs. | 1 | 3 | 5 | 7 | 9 | Total |
|---|---|---|---|---|---|---|
| Alkylates Produced From 80/20 HF/Sulfolane: 90° F./300 ml Catalyst | | | | | | |
| % Conversion | 100.00 | 100.00 | 100.00 | 100.00 | 100.00 | ** |
| Fluorides | 0.54 | 0.30 | 0.30 | 0.35 | 0.44 | 0.05 |
| Lights | 15.21 | 14.94 | 14.89 | 15.23 | 17.42 | <1 |
| C5+ Alkylate (Wt. % Isobutane-Free Basis) | | | | | | |
| C5–7 | 22.21 | 13.42 | 12.37 | 11.94 | 12.26 | 8.70 |
| C8 | 43.50 | 54.61 | 56.76 | 59.88 | 55.31 | 67.70 |
| C9+ | 18.95 | 17.04 | 15.48 | 12.80 | 15.01 | 22.43 |

TABLE I-continued

| Time, Hrs. | 1 | 3 | 5 | 7 | 9 | Total |
|---|---|---|---|---|---|---|
| TMP | 35.39 | 45.26 | 47.14 | 49.97 | 46.22 | 55.96 |
| DMH | 7.89 | 9.15 | 9.33 | 9.58 | 8.98 | 11.46 |
| TMP/DMH | 4.49 | 4.95 | 5.05 | 5.22 | 5.15 | 4.88 |
| R + M/2 | 89.0 | 91.9 | 92.0 | 92.6 | 92.4 | 91.8 |

Lights = All C2, C3, and C4 components except iC4
Total = Total combined alkylate after iC4/volatiles removed
Pressure: 100 psig
Feed: 9.41/1 isobutane/2-butenes
Temp: 90° F. (+/− 2° F.)
Calculated Contact Time: 19.2 seconds
Calculated Hydrocarbon Rise Velocity: 0.104 ft./sec.

TABLE II

| TOS, Hrs. | 1 | 3 | 5 | 7 | 9 | Total |
|---|---|---|---|---|---|---|
| 80/20 HF/Sulfolane + Ideal Feeds: Static Bed: 90° F./100 mL Catalyst | | | | | | |
| % Converted | 100.0 | 100.0 | 99.4 | 99.4 | 81.0 | ** |
| Fluorides | 3.79 | 2.03 | 3.60 | 5.98 | 30.9 | ** |
| Lights | 5.68 | 3.32 | 5.50 | 7.70 | 49.32 | <1 |
| C5+ Alkylate (Wt. % Isobutane-Free Basis) | | | | | | |
| C5-7 | 15.26 | 13.59 | 14.74 | 14.56 | 7.36 | 9.74 |
| C8 | 56.18 | 62.74 | 60.20 | 53.40 | 24.47 | 65.30 |
| C9+ | 22.54 | 18.30 | 18.99 | 23.41 | 17.26 | 23.15 |
| TMP | 46.04 | 51.65 | 49.27 | 43.36 | 19.38 | 53.35 |
| DMH | 9.95 | 10.91 | 10.77 | 9.95 | 4.99 | 11.77 |
| TMP/DMH | 4.63 | 4.73 | 4.57 | 4.36 | 3.88 | 4.53 |
| R + M/2 | 91.1 | 91.7 | 91.2 | 90.4 | 85.9 | 91.4 |

Lights = All C2, C3, and C4 components except iC4
Total = Total combined alkylate after iC4/volatiles removed
Feed: 9.23/1 isobutane/2-butenes
Pressure: 100 psig
Temp: 90.0 (+/− 1° F.)
Calculated Contact time: 6.4 seconds
Calculated Hydrocarbon Rise Velocity: 0.104 ft./sec.

TABLE III

| TOS, Hrs. | 0.5 | 1 | 3 | 5 | 7 | 9 | Total |
|---|---|---|---|---|---|---|---|
| 60/40 HF/Sulfolane + Ideal Feeds: Static Bed: 90° F./300 mL Catalyst | | | | | | | |
| % Converted | 100.0 | 100.0 | 100.0 | 100.0 | 100.0 | 100.0 | ** |
| Fluorides | 0.75 | 2.18 | 2.09 | 0.64 | 0.88 | 4.50 | ** |
| Lights | 13.11 | 16.19 | 15.47 | 13.94 | 13.31 | 21.23 | <1 |
| C5+ Alkylate (Wt. % Isobutane-Free Basis) | | | | | | | |
| C5-7 | 13.21 | 12.66 | 12.49 | 12.64 | 12.82 | 14.30 | 13.14 |
| C8 | 54.45 | 54.27 | 52.34 | 53.83 | 52.22 | 44.05 | 64.89 |
| C9+ | 19.12 | 16.75 | 19.33 | 19.07 | 21.34 | 19.92 | 23.40 |
| TMP | 44.93 | 44.46 | 42.60 | 43.71 | 41.93 | 35.15 | 52.06 |
| DMH | 9.36 | 9.81 | 9.74 | 9.97 | 10.06 | 8.83 | 12.73 |
| TMP/DMH | 4.80 | 4.53 | 4.37 | 4.39 | 4.17 | 3.98 | 91.0 |
| R + M/2 | 91.7 | 91.8 | 91.3 | 91.3 | 90.8 | 90.7 | 90.99 |

Lights = All C2, C3, and C4 components except iC4
Total = Total combined alkylate after iC4/volatiles removed
Feed: 9.43/1 isobutane/2-butenes
Pressure: 100 psig
Temp: 90.0 (+/− 1° F.)
Calculated Contact Time: 17.5 seconds
Calculated Hydrocarbon Rise Velocity: 0.114 ft./sec.

Table IV

| TOS, Hrs. | 1 | 2 | 3 | 4 | Total |
|---|---|---|---|---|---|
| 60/40 HF/Sulfolane + Ideal Feeds: Static Bed: 90° F./100 mL Catalyst | | | | | |
| % Converted | 99.9 | 98.3 | 98.2 | 91.4 | ** |
| Fluorides | 5.99 | 13.07 | 22.07 | 26.43 | ** |
| Lights | 7.74 | 15.86 | 26.67 | 33.46 | |
| C5+ Alkylate (Wt. % Isobutane-Free Basis) | | | | | |
| C5-7 | 6.59 | 8.12 | 10.39 | 10.30 | |
| C8 | 61.89 | 51.35 | 39.05 | 28.26 | NOT EVALUATED |
| C9+ | 23.56 | 24.23 | 23.40 | 28.65 | |
| TMP | 50.48 | 41.24 | 31.14 | 21.94 | |
| DMH | 11.22 | 9.94 | 7.67 | 6.20 | |
| TMP/DMH | 4.50 | 4.15 | 4.06 | 3.54 | |
| R + M/2 | 90.7 | 89.2 | 87.9 | 86.0 | |

Lights = All C2, C3, and C4 components except iC4
Feed: 8.82/1 isobutane/2-butenes
Pressure: 100 psig
Temp: 90.0 (+/− 1° F.)
Calculated Contact Time: 6.4 seconds
Calculated Hydrocarbon Rise Velocity: 0.104 ft./sec.

TABLE V

| TOS, Hrs. | 1 | 3 | 5 | 7 | 9 | Total |
|---|---|---|---|---|---|---|
| 50/50 HF/Sulfolane + Ideal Feeds: Static Bed: 90° F./300 mL Catalyst | | | | | | |
| % Converted | 95.1 | 94.8 | 93.8 | 94.3 | 83.3 | ** |
| Fluorides | 3.31 | 1.68 | 4.54 | 4.82 | 14.24 | 0.0 |
| Lights | 5.60 | 5.11 | 8.01 | 8.26 | 29.08 | <0.1 |
| C5+ Alkylate (Wt. % Isobutane-Free Basis) | | | | | | |
| C5-7 | 15.44 | 10.56 | 16.06 | 15.14 | 11.62 | 4.6 |
| C8 | 52.42 | 53.58 | 49.13 | 44.05 | 29.40 | 49.35 |
| C9+ | 26.27 | 30.50 | 26.34 | 31.72 | 28.97 | 44.68 |
| TMP | 40.94 | 41.92 | 37.75 | 33.59 | 22.11 | 38.29 |

TABLE V-continued

| TOS, Hrs. | 1 | 3 | 5 | 7 | 9 | Total |
|---|---|---|---|---|---|---|
| DMH | 11.44 | 11.68 | 11.20 | 10.30 | 7.16 | 10.92 |
| TMP/DMH | 3.58 | 3.59 | 3.37 | 3.26 | 3.09 | 3.51 |
| R + M/2 | 89.7 | 89.6 | 89.6 | 88.9 | 88.3 | 87.9 |

Lights = All C2, C3, and C4 components except iC4
Feed: 10.8/1 isobutane/2-butenes
Pressure: 100 psig
Temp: 90.0 (+/− 1° F.)
Total: Total combined alkylate after iC/volatiles removed.
Calculated Contact Time: 16.9 seconds
Calculated Hydrocarbon Rise Velocity: 0.118 ft./sec.

TABLE VI

| TOS, Hrs. | 2 | 3 | 4 | 5 | 6 | Total |
|---|---|---|---|---|---|---|
| 50/50 HF/Sulfolane + Ideal Feeds: Static Bed: 90° F./200 mL Catalyst | | | | | | |
| % Converted | 91.1 | 89.9 | 88.6 | 86.4 | 72.8 | ** |
| Fluorides | 10.04 | 10.16 | 24.05 | 50.61 | 62.46 | ** |
| Lights | 17.88 | 17.33 | 32.12 | 59.64 | 80.53 | |
| C5+ Alkylate (Wt. % Isobutane-Free Basis) | | | | | | |
| C5–7 | 13.92 | 12.03 | 7.67 | 4.11 | 2.05 | |
| C8 | 34.03 | 34.78 | 27.09 | 16.19 | 8.53 | NOT |
| C9+ | 33.45 | 34.85 | 32.01 | 19.30 | 8.47 | EVAL- |
| TMP | 25.55 | 26.26 | 20.53 | 12.18 | 6.39 | UATED |
| DMH | 8.33 | 8.34 | 6.38 | 3.91 | 2.07 | |
| TMP/DMH | 3.07 | 3.15 | 3.22 | 3.12 | 3.09 | |
| R + M/2 | 88.2 | 88.0 | 87.7 | 87.7 | 88.3 | |

Lights = All C2, C3, and C4 components except iC4
Feed: 9.55/1 isobutane/2-butenes
Pressure: 100 psig
Temp: 90.0 (+/− 1° F.)
Calculated Contact Time: 11.3 seconds
Calculated Hydrocarbon Rise Velocity: 0.118 ft./sec.

While this invention has been described in terms of the presently preferred embodiment, reasonable variations and modifications are possible by those skilled in the art. Such variations and modifications are within the scope of the described invention and the appended claims.

That which is claimed is:

1. A process for reacting a mixture of hydrocarbons, including olefins and isoparaffins, in the presence of a catalyst comprising sulfolane, acid soluble oil and hydrofluoric acid, wherein the sulfolane in said catalyst is in the range of from 10 weight percent to 50 weight percent, and said acid soluble oil in said catalyst is in the range of from 0.4 weight percent to 8 weight percent, which said catalyst passes through a cyclic path defined by a reactor, a settler vessel, a heat exchanger and a return all of which are operatively connected in series and in fluid flow communication, said cyclic path having a geometry which permits the natural circulation of said catalyst through said cyclic path solely by energy imparted to said catalyst by flowing hydrocarbons and density differential in said cyclic path, the process comprising the steps of:

introducing said mixture into said reactor containing said catalyst;

passing an alkylate reaction effluent resulting from the reaction of said olefins and isoparaffins within said reactor and including hydrocarbons and said catalyst from said reactor to said settler wherein a phase separation occurs so as to produce a hydrocarbon phase and a catalyst phase;

passing said catalyst phase to said heat exchanger whereby energy is removed from said catalyst phase by indirect heat exchange to produce a cooled catalyst; and utilizing said cooled catalyst as said catalyst contained in said reactor.

2. A process as recited in claims wherein said reactor defines a vertically extending reaction zone having a volume and an effective length-to-diameter ratio of greater than about 5 to 1.

3. A process as recited in claim 2 wherein a contact time of said mixture with said catalyst is at least about 5 seconds.

4. A process as recited in claim 1 wherein a contact time of said mixture with said catalyst is at least about 5 seconds.

5. A process as recited in claim 1 wherein the reaction conditions within said rector are maintained at a temperature in the range of from about 0° F. to about 150° F. and a pressure in the range of from about ambient pressure to about 15 atmospheres but sufficient to maintain liquid phase conditions.

6. A process as recited in claim 1 wherein the molar ratio of isoparaffin-to-olefin in said mixture is in the range of from about 2:1 to about 25:1.

7. A process for reacting a mixture including olefin hydrocarbons with isoparaffin hydrocarbons within a vertically extended reaction zone, having a lower portion, an upper portion and a volume, in the presence of a catalyst comprising sulfolane, acid soluble oil and hydrofluoric acid, wherein the sulfolane in said catalyst is in the range of from 10 weight percent to 50 weight percent, and said acid soluble oil in said catalyst is in the range of from 0.4 weight percent to 8 weight percent, comprising the steps of:

introducing said mixture into said lower portion of said reaction zone containing said catalyst at a volumetric rate such that a contact time of said mixture with said catalyst is at least about 10 seconds;

passing an alkylate reaction effluent including hydrocarbons and said catalyst from said upper portion of said reaction zone to a settling zone wherein a phase separation occurs so as to produce a hydrocarbon phase and a catalyst phase;

cooling said catalyst phase to produce a cooled catalyst; and utilizing said cooled catalyst as said catalyst within said reaction zone.

8. A process as recited in claim 7 wherein said volume of said vertically extended reaction zone is defined by a riser-reactor having an effective length-to-diameter ratio of greater than about 5 to 1.

9. A process as recited in claim 7 wherein a contact time of said mixture with said catalyst is at least about 10 seconds.

10. A process as recited in claim 7 wherein the reaction conditions within said reaction zone are maintained at a temperature in the range of from about 0° F. to about 150° F. and a pressure in the range of from about ambient pressure to about 15 atmospheres but sufficient to maintain liquid phase conditions.

11. A process as recited in claim 7 wherein the molar ratio of isoparaffin-to-olefin in said mixture is in the range of from about 2:1 to about 25:1.

12. A process for reacting a mixture including olefin hydrocarbons with isoparaffin hydrocarbons within a reaction zone defined by a riser-reactor, having a lower portion, an upper portion, and an effective length-to-diameter ratio of greater than about 5 to 1, in the presence of a catalyst comprising sulfolane, acid soluble oil and hydrofluoric acid, wherein the sulfolane in said catalyst is in the range of from 10 weight percent to 50 weight percent, and said acid soluble oil in said catalyst is in the range of from 0.4 weight percent to 8 weight percent, comprising the steps of:

introducing said mixture into said lower portion of said reaction zone containing said catalyst at a rate such that the volumetric ratio of said catalyst to said mixture within said reaction zone is in the range of from about 1 to about 9;

passing an alkylate reaction effluent including hydrocarbons and said catalyst from said upper portion of said reaction zone to a settling zone wherein a phase separation occurs so as to produce a hydrocarbon phase and a catalyst phase;

cooling said catalyst phase to produce a cooled catalyst; and utilizing said cooled catalyst as said catalyst within said reaction zone.

13. A process as recited in claim 12 wherein a contact time of said mixture with said catalyst is at least about 10 seconds.

14. A process as recited in claim 12 wherein the reaction conditions within said reaction zone are maintained at a temperature in the range of from about 0° F. to about 150° F. and a pressure in the range of from about ambient pressure to about 15 atmospheres but sufficient to maintain liquid phase conditions.

15. A process as recited in claim 12 wherein the molar ratio of isoparaffin-to-olefin in said mixture is in the range of from about 2:1 to about 25:1.

16. A process for reacting a mixture of hydrocarbons, including olefins and isoparaffins, in the presence of a catalyst, consisting essentially of sulfolane in the range of from 10 weight percent to 50 weight percent, acid soluble oil in the range of from 0.4 weight percent to 8 weight percent and hydrofluoric acid, which said catalyst passes through a cyclic path defined by a reactor, a settler vessel, a heat exchanger and a return all of which are operatively connected in series and in fluid flow communication, said cyclic path having a geometry which permits the natural circulation of said catalyst through said cyclic path solely by energy imparted to said catalyst by flowing hydrocarbons and density differential in said cyclic path, the process comprising the steps of:

introducing said mixture into said reactor containing said catalyst;

passing an alkylate reaction effluent resulting from the reaction of said olefins and isoparaffins within said reactor and including hydrocarbons and said catalyst from said reactor to said settler wherein a phase separation occurs so as to produce a hydrocarbon phase and a catalyst phase;

passing said catalyst phase to said heat exchanger whereby energy is removed from said catalyst phase by indirect heat exchange to produce a cooled catalyst; and utilizing said cooled catalyst as said catalyst contained in said reactor.

17. A process as recited in claim 16 wherein said reactor defines a vertically extending reaction zone having a volume and an effective length-to-diameter ratio of greater than about 5 to 1.

18. A process as recited in claim 17 wherein a contact time of said mixture with said catalyst is at least about 5 seconds.

19. A process as recited in claim 18 wherein the weight percent ratio of sulfolane in said catalyst is in the range of from about 2.5 weight percent to about 50 weight percent.

20. A process as recited in claim 16 wherein a contact time of said mixture with said catalyst is at least about 5 seconds.

21. A process as recited in claim 16 wherein the reaction conditions within said reactor are maintained at a temperature in the range of from about 0° F. to about 150° F. and a pressure in the range of from about ambient pressure to about 15 atmospheres but sufficient to maintain liquid phase conditions.

22. A process as recited in claim 16 wherein the molar ratio of isoparaffin-to-olefin in said mixture is in the range of from about 2:1 to about 25:1.

23. A process for reacting a mixture including olefin hydrocarbon with isoparaffin hydrocarbons within a vertically extended reaction zone, having a lower portion, an upper portion and a volume, in the presence of a catalyst consisting essentially of sulfolane in the range of from 10 weight percent to 50 weight percent, acid soluble oil in the range of from 0.4 weight percent to 8 weight percent and hydrofluoric acid, comprising the steps of:

introducing said mixture into said lower portion of said reaction zone containing said catalyst at a volumetric rate such that a contact time of said mixture with said catalyst is at least about 10 seconds;

passing an alkylate reaction effluent including hydrocarbons and said catalyst from said upper portion of said reaction zone to a settling zone wherein a phase separation occurs so as to produce a hydrocarbon phase and a catalyst phase;

cooling said catalyst phase to produce a cooled catalyst; and utilizing said cooled catalyst as said catalyst within said reaction zone.

24. A process as recited in claim 23 wherein said volume of said vertically extended reaction zone is defined by a riser-reactor having an effective length-to-diameter ratio of greater than about 5 to 1.

25. A process as recited in claim 24 wherein the weight percent of sulfolane in said catalyst is in the range of from about 2.5 weight percent to about 50 weight percent.

26. A process as recited in claim 23 wherein a contact time of said mixture with said catalyst is at least about 10 seconds.

27. A process as recited in claim 23 wherein the reaction conditions within said reaction zone are maintained at a temperature in the range of from about 0° F. to about 150° F. and a pressure in the range of from about ambient pressure to about 15 atmospheres but sufficient to maintain liquid phase conditions.

28. A process as recited in claim 23 wherein the molar ratio of isoparaffin-to-olefin in said mixture is in the range of from about 2:1 to about 25:1.

29. A process for reacting a mixture including olefin hydrocarbons with isoparaffin hydrocarbons within a reaction zone defined by a riser-reactor, having a lower portion, an upper portion, and an effective length-to-diameter ratio of greater than about 5 to 1, in the presence of a catalyst consisting essentially of sulfolane in the range of from 10 weight percent to 50 weight percent, acid soluble oil in the range of from 0.4 weight percent to 8 weight percent and hydrofluoric acid, comprising the steps of:

introducing said mixture into said lower portion of said reaction zone containing said catalyst at a rate such that the volumetric ratio of said catalyst to said mixture within said reaction zone is in the range of from about 1 to about 9;

passing an alkylate reaction effluent including hydrocarbons and said catalyst from said upper portion of said reaction zone to a settling zone wherein a phase separation occurs so as to produce a hydrocarbon phase and a catalyst phase;

cooling said catalyst phase to produce a cooled catalyst; and utilizing said cooled catalyst as said catalyst within said reaction zone.

30. A process as recited in claim 29 wherein a contact time of said mixture with said catalyst is at least about 10 seconds.

31. A process as recited in claim 30 wherein the weight percent of sulfolane in said catalyst is in the range of from about 2.5 weight percent to about 50 weight percent.

32. A process as recited in claim 29 wherein the reaction conditions within said reaction zone are maintained at a temperature in the range of from about 0° F. to about 150° F. and a pressure in the range of from about ambient pressure to about 15 atmospheres but sufficient to maintain 5 liquid phase conditions.

33. A process as recited in claim 29 wherein the molar ratio of isoparaffin-to-olefin in said mixture is in the range of from about 2:1 to about 25:1.

* * * * *